(12) United States Patent
Heinzler

(10) Patent No.: US 8,979,914 B2
(45) Date of Patent: Mar. 17, 2015

(54) IRRADIATION DEVICE WITH ERGONOMIC ADAPTATION OPTIONS

(75) Inventor: Marcus Heinzler, Hausen O.V. (DE)

(73) Assignee: Herbert Waldman GmbH & Co. KG, Villingen-Schwenningen (DE)

(*) Notice: Subject to any disclaimer, the term of this patent is extended or adjusted under 35 U.S.C. 154(b) by 859 days.

(21) Appl. No.: 13/229,384

(22) Filed: Sep. 9, 2011

(65) Prior Publication Data

US 2012/0089204 A1    Apr. 12, 2012

(30) Foreign Application Priority Data

Oct. 6, 2010    (DE) .................. 10 2010 047 494

(51) Int. Cl.
*A61N 5/06*    (2006.01)

(52) U.S. Cl.
CPC ....... *A61N 5/0613* (2013.01); *A61N 2005/0633* (2013.01); *A61N 2005/0642* (2013.01); *A61N 2005/0661* (2013.01)
USPC .............. 607/88; 362/418; 362/427; 362/431

(58) Field of Classification Search
CPC ....... F21V 21/26; F21V 21/116; F21V 21/30; A61N 5/062
USPC .............................. 607/88; 362/418, 427, 431
See application file for complete search history.

(56) References Cited

U.S. PATENT DOCUMENTS

| | | | |
|---|---|---|---|
| 2003/0103357 A1* | 6/2003 | Drake et al. | 362/403 |
| 2003/0216795 A1 | 11/2003 | Harth et al. | |
| 2010/0232148 A1* | 9/2010 | Sharpley et al. | 362/183 |
| 2011/0095902 A1* | 4/2011 | Mandel | 340/815.65 |

FOREIGN PATENT DOCUMENTS

| | | |
|---|---|---|
| DE | 8327343 | 1/1984 |
| DE | 3602940 | 7/1986 |
| DE | 90 12 814.1 | 12/1990 |
| DE | 297 02 785 | 6/1997 |
| DE | 20317167 | 1/2004 |
| DE | 203 17 167 | 2/2004 |
| DE | 20 2009 013 594 | 1/2010 |
| GB | 2 082 747 | 8/1981 |
| GB | 2 082 747 | 3/1982 |
| GM | 79 25 806 | 2/1980 |

(Continued)

OTHER PUBLICATIONS

Chinese Office Action, Appln. Serial No. 201110251652.9, mailed Jan. 13, 2014, 2 pages—English.

(Continued)

*Primary Examiner* — William Thomson
*Assistant Examiner* — Jeffrey Lipitz
(74) *Attorney, Agent, or Firm* — Andrew F. Young, Esq.; Lackenbach Siegel, LLP

(57) ABSTRACT

An irradiation device for irradiating of body parts of a patient is provided, with a carrier system which provides a basic framework of the irradiation device with at least one light head with a light source for the irradiation, and a control element for operating the irradiation device. The irradiation device moreover includes a separate control module that is connected with the carrier system with at least one control for controlling the at least one light head. Innovative assembly and connection arrangements aid rapid and secure positioning.

10 Claims, 12 Drawing Sheets

(56) References Cited

FOREIGN PATENT DOCUMENTS

| WO | WO 02/098508    | 12/2002 |
| WO | WO 2005/030317  | 4/2005  |
| WO | WO 2006/048162  | 5/2006  |
| WO | WO 2009/133385  | 11/2009 |

OTHER PUBLICATIONS

German Office Action, Appln. Serial No. 10 2010 047 494.0, mailed Jun. 20, 2012, 6 pages—German, 3 pages—English.
German Search Report, Appln. Serial No. 11173713.6 mailed Jan. 31, 2012, 6 pages—German, 2 pages—English.

* cited by examiner

IRRADIATION DEVICE WITH ERGONOMIC ADAPTATION OPTIONS

CROSS REFERENCE TO RELATED APPLICATIONS

This application relates to and claims priority from German Ser. No. 10 2010 047 494.0 filed Oct. 6, 2010, the entire contents of which are incorporated herein by reference.

FIGURE SELECTED FOR PUBLICATION

FIG. 2

BACKGROUND OF THE INVENTION

1. Field of the Invention

The present invention relates to an irradiation device for irradiating body parts of a patient with a carrier system, at least one light head, and a control element.

2. Description of the Related Art

Industrial applications of irradiation devices for irradiation of body parts of a patient are known from the art as so-called partial-body therapy units for the irradiation of hands, feet, or the chest, the back, breech, knee, or lower leg within the scope of so-called UV phototherapy. The known therapy units as a rule consist of an equipment carrier which designed as a trolley. Attached on the equipment carrier are light heads, so-called treatment heads, which in each case have a light source as well as ballasts for their control. The treatment heads are consequently very heavy and are therefore firmly bolted or statically locked with the equipment carrier as a rule. The treatment heads are normally aligned once during the assembly of the unit, by using special tools. With these units it is therefore not possible to adjust the treatment heads and/or the entire unit individually for the therapy of a single patient, and thus perform an ergonomic adaptation. The patient rather has to adapt to the irradiation device and must accordingly be positioned relative to the unit. This means that the patient must remain in an uncomfortable position for the entire time of the treatment, if necessary, which can sometimes last as long as several minutes.

Due to the firmly integrated treatment heads, the therapy unit can moreover not be adapted to different types of treatment, since it is not possible to align the treatment heads appropriately. While the emission surface for the irradiation of hands should be aligned as level as possible, the emission surface for facial treatment should essentially have a steep angle of inclination in order to be parallel to the face. A change in the alignment of the treatment heads is only possible by using corresponding tools and is also conditional upon sufficient pivotability of the treatment heads. Due to the required complexity, it can therefore not be individually adapted to the respective patient.

A further disadvantage results from the controls and control elements respectively integrated in the individual treatment heads as well as their decentralized configuration resulting therefrom, whereby the operation of the entire therapy unit becomes complicated. The consequence is that the user requires to have direct access to the respective treatment heads in order to operate it. Especially treatment heads that are arranged in a lower area of the therapy unit require that the user assumes a stooped posture in order to operate the unit. Where therapy units have a particular height and where treatment buttons are provided in this area, particularly shorter people have significant problems in operating these control elements as well as taking readings of corresponding displays. In addition, with therapy units known from prior art it is necessary that the user has to stand in front of the unit in order to operate it and to operate the control elements arranged on the treatment heads. It is therefore not possible to place the patient in front of the unit before it is operated. Any adjustments must have rather been completely finalized in advance.

Depending upon therapy, it may be required to replace the treatment heads and use with treatment heads that have a different light source, such as UV-A and UV-B light sources. With the known equipment as previously described, this would require using additional tools. Such replacement would moreover be possible only using significant force, because of the considerable weight of the treatment heads already mentioned previously.

Because each treatment head has its own control element and a control panel, in addition not just the operation of the individual control elements is inconvenient, but rather also a correspondingly higher number of individual control elements and/or operating elements is necessary, as a result of which a high amount of resources and expenditure is necessary.

Accordingly, there is a need for an improved irradiation device for irradiating body parts of a patient with a carrier system, at least one light head, and a control element

ASPECTS AND SUMMARY OF THE INVENTION

In response, it is now recognized as an object of the invention therefore to provide an irradiation device that can be individually and ergonomically adapted to the patient to be treated, so that the patient can be placed in front of the unit in a comfortable position. In addition, the irradiation device must also be adaptable to the different types of treatments and therapies and also be easy and convenient to operate.

In brief an aspect of the invention is to provide an irradiation device for irradiating body parts of the patient is provided, which comprises a carrier system that provides a basic framework of the irradiation device.

In another aspect of the invention an irradiation device for irradiating of body parts of a patient is provided, with a carrier system which provides a basic framework of the irradiation device with at least one light head with a light source for the irradiation, and a control element for operating the irradiation device. The irradiation device moreover includes a separate control module that is connected with the carrier system with at least one control for controlling the at least one light head. Innovative assembly and connection arrangements aid rapid and secure positioning.

The irradiation device moreover contains at least one light head with a light source for the irradiation, and a control element for operating the irradiation device. The irradiation device moreover includes a separate control module with at least one control for controlling the at least one light head, where said separate control module is connected with the carrier system.

Consequently, the control of one or multiple light heads is designed as a common separate device and is not integrated in the respective light heads. Such type of control inter alia includes ballasts, in particular magnetic ballasts, and further electronic components for the control of the light sources in the at least one light head. This offers the possibility to significantly reduce the weight of the respective light head and to integrate the said components into the independent, separate control module, and to combine them there. Therefore, a single and common control of multiple light heads can be provided. Preferably, because of the combination of the individual components and controls they can be used together, which in turn preserves resources.

The separate control module can moreover be designed as a control cabinet or a rack. Control cabinet specifically means a housing which contains the components and electronic components which are assigned to the control for controlling the light heads. The control cabinet essentially has a stretched, rectangular structure, for example. The control cabinet is preferably designed like a panel with a small depth relative to its width and a large height. Preferably, the control cabinet preferably has at least one level front side which is facing the patient in the operational state.

Pursuant to a further embodiment, the at least one light head has a modular design and is detachably connected with the control module. This means that the light is exclusively arranged on the control module, but does not have its own connection to the carrier system. Furthermore, because of its modular design and the detachable connection, the light head is arranged on the control module so it can be replaced, and can be removed or replaced as required. For this purpose, the detachable connection is preferably designed such that the light head can be removed and/or inserted without using tools, but is adequately fixed for safe operation, however.

According to another embodiment, the control module is connected relative to the carrier system pivotable with the carrier system about a first pivot axis. In this manner, the control module can be pivoted relative to the carrier system in order to adapt the irradiation device individually to the patient undergoing the therapy. The carrier system can essentially have a U-shaped design, for example, wherein the pivot axis is supported on the two outer ends of the two legs of the U-shaped carrier system so that it connects the two ends to each other.

Preferably, the at least one light head his pivotable relative to the control module about a second pivot axis, in each case. This facilitates improved, universal applicability of the respective light head, since it can be pivoted into the optimal position for the respective application. If the back of the hand of a patient placed in front of the unit is to be irradiated, for example, then the light head can be pivoted such that its direction of radiation is aligned parallel to the hand, for example. If, on the other hand, the face of the patient is to be irradiated, then the direction of radiation can be rotated into the desired direction by pivoting the light head.

The first pivot axis and the respective second pivot axis are preferably essentially aligned parallel to one another. This facilitates a particularly advantageous and flexible adaptation of the irradiation device to the different body sizes of the patients undergoing therapy. Both the first as well as also the second pivot axis can be essentially horizontally aligned in their operating status, for example.

Pursuant to a further embodiment, the at least one light head is communicatively connected with the separate control module for exchange of information. The exchange of information between the light head and the control module is particularly important to take into account the type of lamp used, in order to exclude a malfunction or incorrect radiation doses and to ensure the patient's safety.

Because of the option of being able to replace the at least one light head, the control module is preferably designed such that it can identify the respective light head. This includes the identification of the slot where the respective light head is arranged as well as the ability to read out a storage medium provided in the light head. In this storage medium, at least one of the following specifications is stored, for example: component parts of the lamp, i.e. type of light source, intensity, operating time and/or serial number of the respective light head. Naturally, also other or additional specifications can have been stored.

These specifications are preferably read out by means of a bus system at predefined times, at regular intervals, or after fitting a new light head onto the control module.

According to a preferred embodiment, the first pivot axis runs essentially through a center of gravity of the control module. The torques can thus be reduced because of the own weight of the control module, and the stability of the irradiation device can be increased.

Pursuant to another embodiment, the carrier system can be designed mobile so that the irradiation device can traverse. This facilitates particularly easy handling as well as universal applicability of the irradiation device.

The at least one light head is preferably respectively connected by means of detachable plug-and-socket devices with the control module.

For this purpose, the control module has corresponding receptacles in the form of plug-in places for inserting at least one light head. If several of these plug-in places exist, then the one or the several light heads can be preferably placed onto these in any combination. The detachable plug-and-socket devices can be combined with further form-closed and/or force-closed type of connections. Preferably, a combined connection for inserting and subsequently locking the light head in place by means of pivoting the light head pursuant to FIGS. 1 to 12 can be provided.

Pursuant to a further embodiment, the control element of the irradiation device is connected pivotable about at least a third pivot axis with the control module. The control element can therefore be moved into different positions, which thus permits individual adaptation for the respective purpose or to the operating personnel. The control element is preferably connected pivotable with the control module via a swivel arm and can engage in defined swivel positions, so that unintentional pivoting is prevented during the operation of the control element. The respective detent mechanism can be designed such that in order to perform the adjustment, the control element or the swivel arm must initially be lifted from a latched position by pivoting the control element and/or the pivot arm into the desired position, for example. The control element and/or the swivel arm will preferably reengage into the desired position on its own.

According to a preferred embodiment, the at least one light head can be pivoted by an angle which is made up from the amount of a swivel angle of the control module about the first pivot axis and an additional 180°. If the pivoting element can therefore be pivoted by up to 20°, then the light head can be pivoted about its second pivot axis by at least 200°. This presents the possibility to operate the light head both for radiation in a first direction as well as also in one direction that is opposite by 180° hereto, even if the control module is additionally pivoted. If the direction of radiation of the light head in a first position for irradiating a foot is vertical to the bottom, for example, then the light head can be pivoted throughout the aforementioned angular range such that the direction of radiation points to the top in the opposite direction.

The at least one light head can include at least one supporting arm for the detachable connection with at least one holder element formed on the control module for partially holding the at least one supporting arm, for example. The holder elements, also designated as holders in the following, are arranged on the previously described front side that is facing the patient during operation, for example.

The supporting arm is preferably U-shaped, wherein a casing of the light head is arranged between the two legs of the U-shaped supporting arm so that it can be pivoted relative to it. A base section of the U-shaped supporting arm which joins the two legs is connected with the control module in the assembled state.

In the assembled state, the base section of the U-shaped supporting arm is preferably connected with the front side facing the patient during operation.

The at least one supporting arm can furthermore include at least one locking lever for the optional engagement of the light head on the control module. The control module has appropriately designed holder elements for this purpose, into which the locking lever can engage by means of a latch lug at least in sections.

In addition, the at least one light head can be fixable optionally relative to the control module by means of a latching arrangement.

The swiveling motion of the light head about the second pivot axis can therefore be optionally arrested by means of the latching arrangement, and the light head can be aligned correspondingly.

The invention furthermore teaches that a light head is proposed, which is designed according to the description provided. Likewise, a rack pursuant to the description is proposed, which consists of at least the carrier system and a control element as well as a control module designed according to the description for holding a correspondingly designed light head.

The above and other aspects, features and advantages of the present invention will become apparent from the following description read in conjunction with the accompanying drawings, in which like reference numerals designate the same elements.

DETAILED DESCRIPTION OF THE PREFERRED EMBODIMENTS

Figure 1:
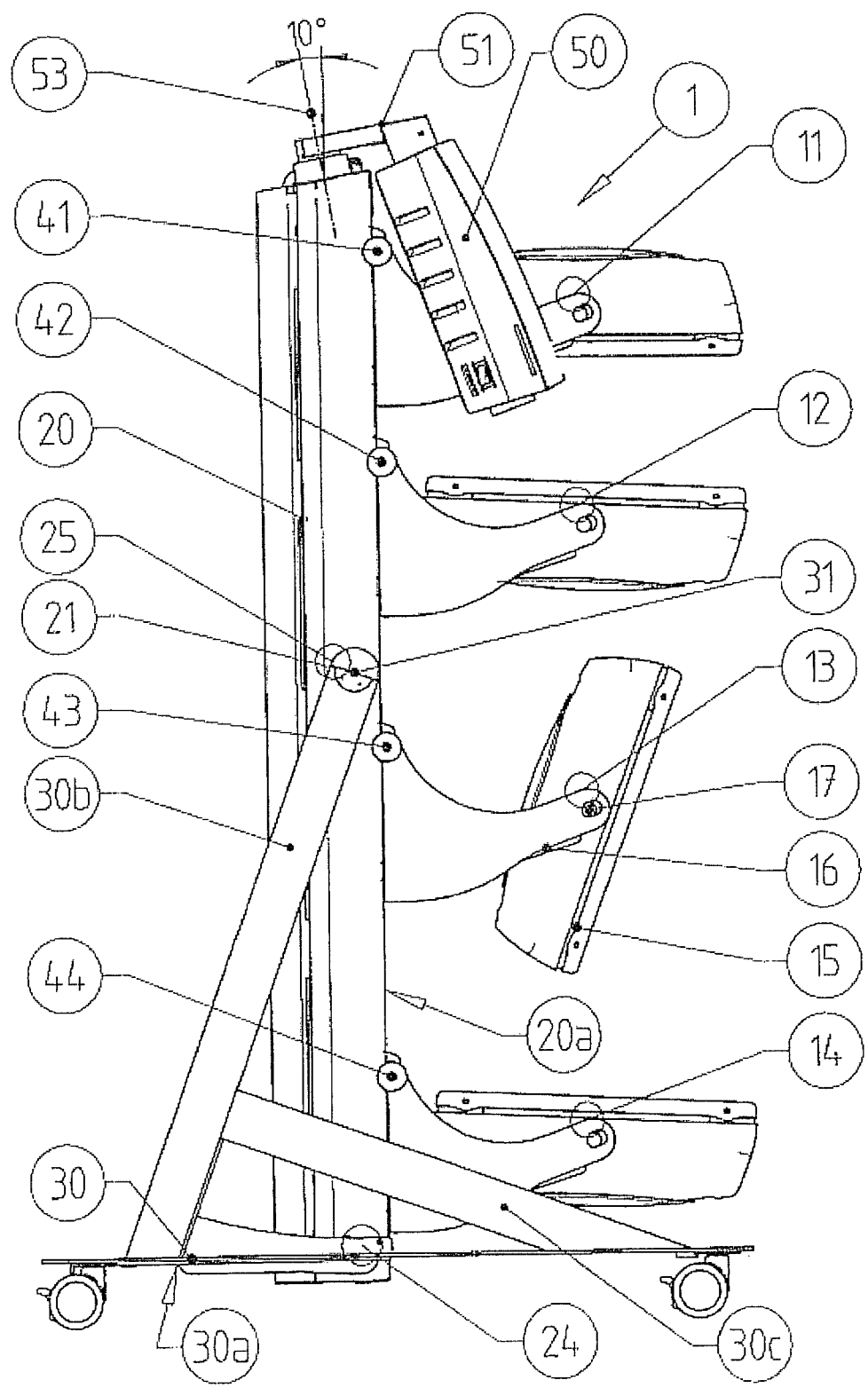
FIG. 1 is a side elevation of an irradiation device as taught by the invention in the vertical position.

Reference will now be made in detail to embodiments of the invention. Wherever possible, same or similar reference numerals are used in the drawings and the description to refer to the same or like parts or steps. The drawings are in simplified form and are not to precise scale. For purposes of convenience and clarity only, directional (up/down, etc.) or motional (forward/back, etc.) terms may be used with respect to the drawings. These and similar directional terms should not be construed to limit the scope of the invention in any manner.

FIG. 1 shows an irradiation device 1 as taught by the invention in the vertical position. The irradiation device 1 comprises a carrier system 30 which provides a basic framework of the irradiation device 1 and carries its further components. In the represented embodiment it is designed traversable by means of castors on a foot 30a of the carrier system 30.

The carrier system 30 has two legs 30b that essentially extend in a vertical direction from the foot 30a, which are respectively supported on the foot 30a by means of a brace 30c. The legs 30b together with the foot 30a form an essentially U-shaped design of the carrier system 30 (see FIGS. 3 and 6). Each of the two legs 30b has a bearing 21 on one end facing away from the foot 30a, in which a first pivot axis 21 is supported. This connects a separate control module 20 pivotable to the carrier system 30, in which controls for controlling of light heads 11, 12, 13, 14 of the irradiation device 1, in particular its ballasts, are arranged. The weight of the individual light heads 11-14 can therefore be reduced. The control module 20 represented is designed as a control cabinet, which is designed with a longitudinal extension aligned vertically and essentially plate-like with a domed rear side. In the represented embodiment, the control module 20 is suspended by means of the first pivot axis 31 at its center of gravity on the carrier system 30, and can be pivoted about the first pivot axis 31. The swiveling motion can be limited in the bearings 21 by stops (not shown), for example. Preferably, a swiveling motion of the control module 20 from the starting position represented in FIG. 1 is possible with a angle of inclination of 0° relative to the perpendicular in a pivoted position pursuant to FIG. 2 with an angle of inclination of 20°, for example, relative to the perpendicular and/or the starting position for an anatomical and ergonomic adaptation to a patient undergoing radiation. The swiveling of the control module 20 can be performed by means of gearing 24 or 25.

The described control module 20, designed as a control cabinet, has a first front side 20a, which in an operating status is facing a patient undergoing radiation. On this front side 20a, multiple holders 41, 42, 43, 44 are arranged for the detachable connection of the modularly designed light heads 11-14 with the control module 20. The represented light heads 11-14 have supporting arms 16, which on one end of the respective light head facing away have pivot pins for insertion into the holders 41-44. After inserting the pivot pins into the holders 41-44 of the control module 20, the respective light head can be swiveled in a downward motion and be connected with a plug-and-socket device located below the pivot pin for the control module 20 and/or detachably engaged into it (see FIG. 5). In the embodiment represented, four holders 41-44 for light heads 11-14 are represented, which can be occupied and combined as desired. Apart from the illustrated assignment of all four holders 41-44, for example, likewise merely one, two, or three of the holders 41-44 can be assigned in any combination, whereby a particularly flexible possibility for combining the light heads 11-14 is obtained. A different center of gravity position of the pivotable control module 20 which is created in this context can be supported by the irreversibility of the gearing 24 or 25. Naturally it is also possible to provide a corresponding irradiation device 1 with a larger or lesser number of holders 41-44 and light heads 11-14.

Each of the light heads 11-14 includes a casing 15 which can be pivoted about a second pivot axis 17 relative to the respective supporting arm 16 and/or the control module 20, as a result of which the light heads 11-14 can be universally adapted individually for the irradiation of highly different body sections.

The irradiation device 1 in addition has a control element 50 for operating the irradiation device 1, particularly for the central control of the light heads 11-14 via the common control element 50. This can be pivoted about a third pivot axis 53 relative to the control module 20. The control element 50 can therefore be pivoted and operated in the vicinity of the front side 20a of the control module 20 pursuant to the FIGS. 1-3. Alternatively, the control element 50 can be pivoted pursuant to FIG. 4 onto a rear side of the irradiation device 1. For this purpose, the control element 50 of the irradiation device 1 can be pivoted by at least 180°. The control element 50 is preferably connected with the control module 20 by means of a swivel arm 51 which is designed to lock into its end positions, so that inadvertent twisting is prevented during operation of the control element 50. In order to adjust the control element 50 and/or the swivel arm 51, it must be lifted out of its detent mechanism and can then subsequently be put into a desired position. A negative tilt of the control element 50 in case of a pivoted control module 20 pursuant to FIG. 2 which could theoretically develop, will be obviated by a tilted arrangement of the third pivot axis 53 as well as by a respective construction of the swivel arm 51. The control element 50 therefore stands at least vertical, even with a tilted control module 20. Any further joints are therefore unnecessary, and the irradiation device 1 can be operated optimally.

Figure 2:
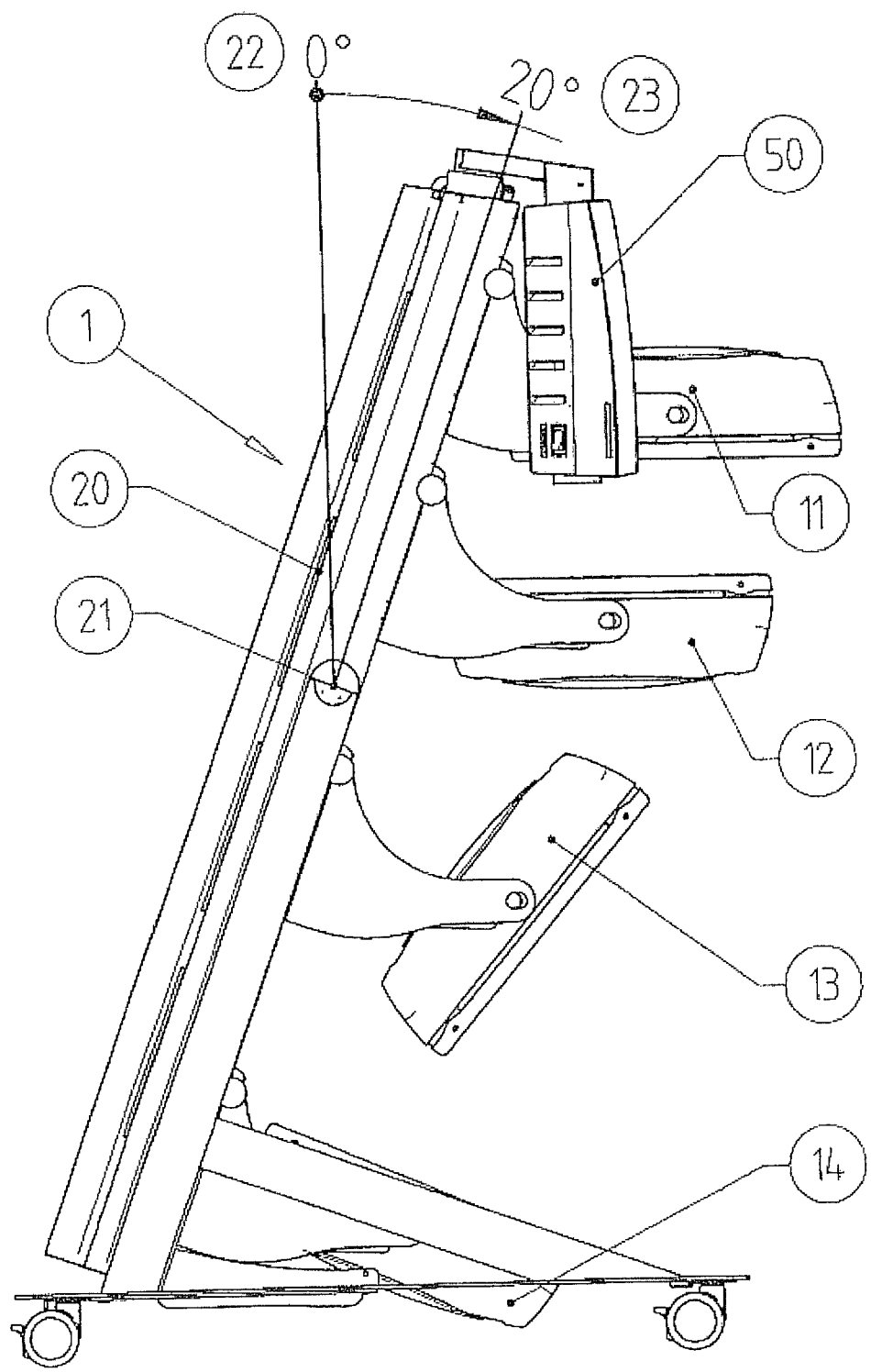
FIG. 2 is the irradiation device as taught by the invention according to FIG. 1, in a pivoted position.

As previously mentioned, FIG. 2 shows the irradiation device 1 as taught by the invention in a pivoted position 23. Because of the tilt of the control module 20 about an angle of inclination of 20° relative to the perpendicular 22, the light heads 11 and 12 arranged above the bearing 21 move towards a patient who is sitting in front of the irradiation device 1.

The light heads 13 and 14 arranged below the bearing 21, are swiveled away from the patient, however. In this manner, the described ergonomic adaptation to the respective patient can be performed. With tall patients, for example, the control module 20 can be brought into the pivoted position 23, whereas with small patients, the control module 20 can be brought into the upright position 22, since in the upright position 22 the distance of the light heads 13 and 14 is reduced for the irradiation of feet to the light heads 11 and 12 for the irradiation of hands.

Figure 3:
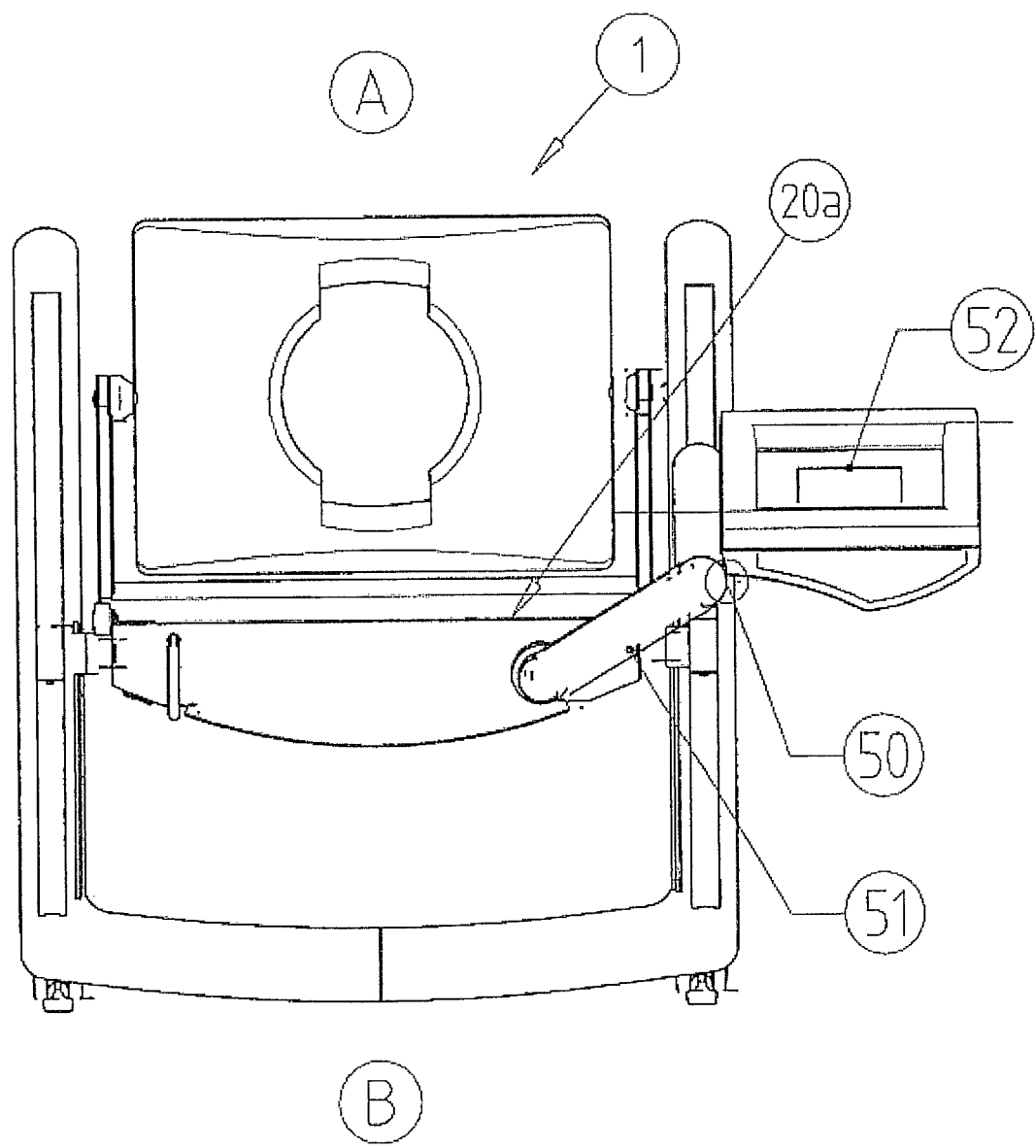
FIG. 3 is the irradiation device as taught by the invention from FIG. 1, in a horizontal position with the control element unfolded.

FIG. 3 shows the irradiation device 1 as taught by the invention from FIG. 1 in a horizontal projection with a folded-out control element 50, the control panel 52 of which faces into the same direction A like the front side 20a.

Figure 4:
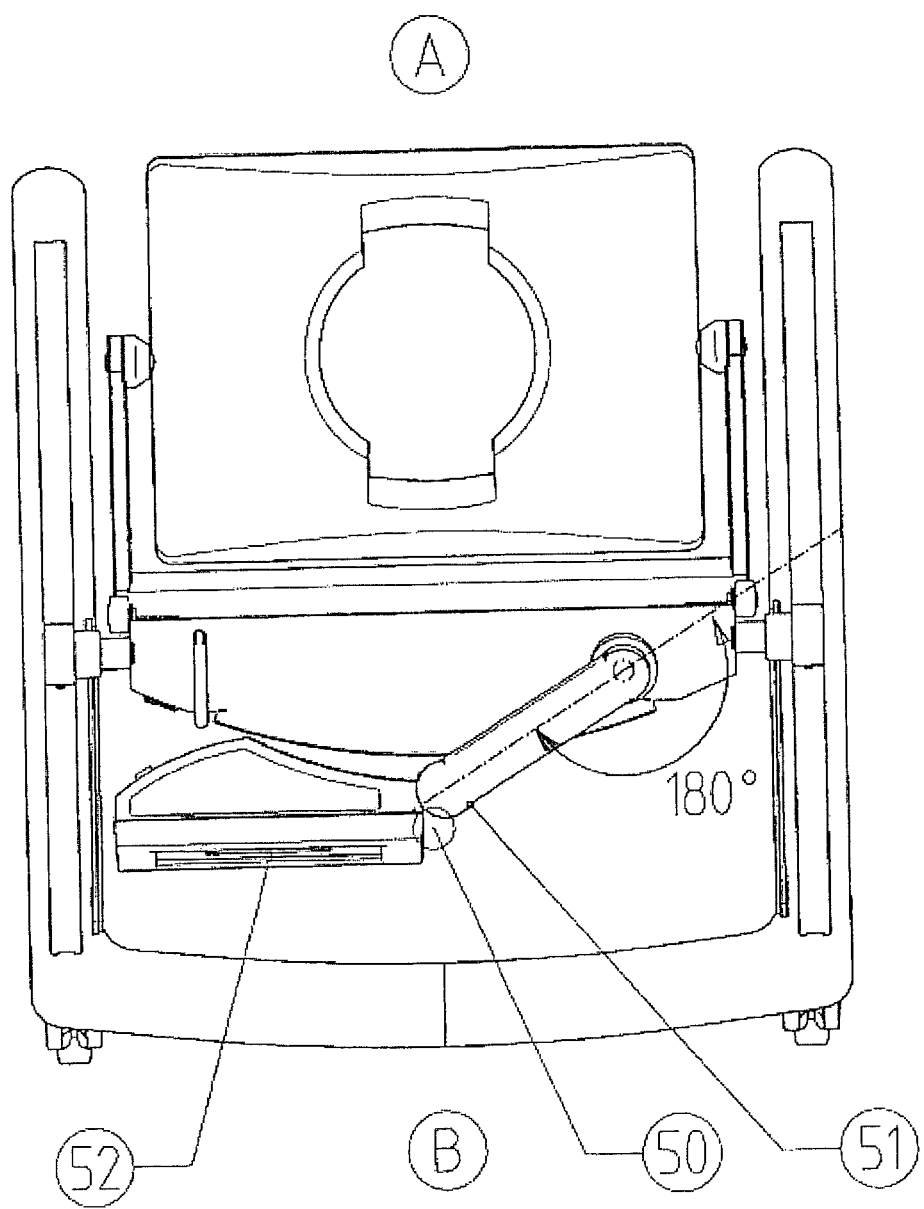
FIG. 4 is the irradiation device as taught by the invention from FIG. 1 in a further horizontal position with the control element folded up.

In FIG. 4, the irradiation device 1 as taught by the invention is represented pursuant to FIGS. 1 and 3, wherein the control element 50 is pivoted by 180° relative to the position shown in FIG. 3 and is thus arranged on a rear side B of the irradiation device 1. The control panel 52 is therefore to be operated from the rear side of the irradiation device 1.

Figure 5:
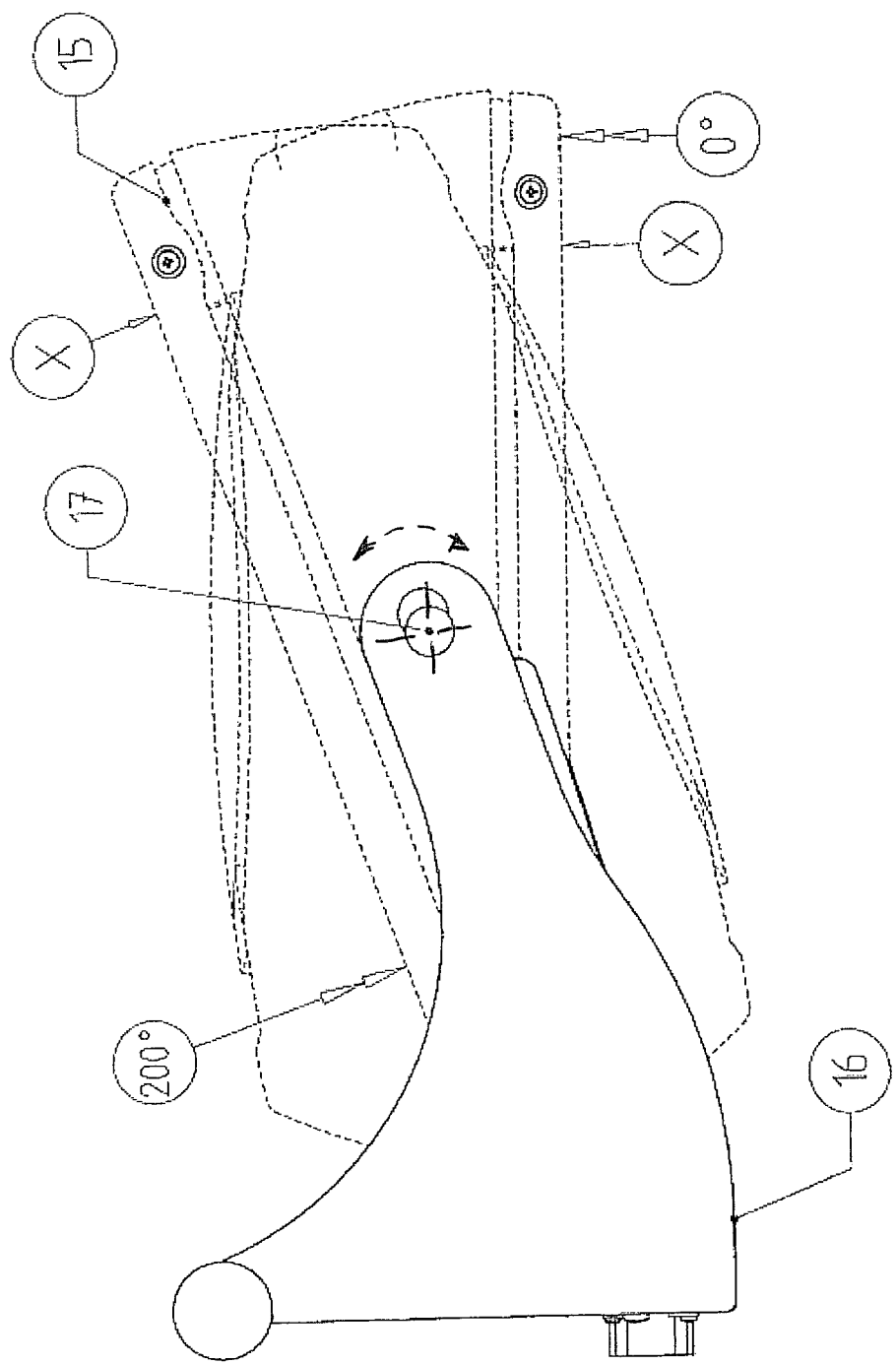
FIG. 5 is a light head as taught by the invention for an irradiation device according to the FIGS. 1-4 in a side elevation of a support arm and casing is shown in two pivoted positions through a pivot turn, from a first position to a second pivoted position.

FIG. 5 shows a light head 12 as taught by the invention for an irradiation device 1 according to one of the FIGS. 1-4 in a lateral view in two different pivoted positions 0° and 200°, which are respectively represented by dashed lines. In each case, an emission surface and/or a light exit surface X of the casing 15 serves as a reference surface, which in a starting position 0° with a swivel angle 0° is directed vertically down and in a position swiveled by 200° faces oblique to the top.

For this purpose, the casing 15 of the light head 12 can be swiveled relative to its supporting arms 16 about the second pivot axis 17. It is thus possible to align the light exit surface X also in the case of the swiveled control module 20 level to the top and/or level to the bottom. This will ensure an optimal adaptation to the ergonomics of the patient and the selected form of treatment. Preferably, the connection cables for the lamps of the light head arranged in the casing 15 are laid through the second pivot axis 17 as well as likewise preferably led covered in the supporting arms 16 up to its end facing away for connecting the control module (cabling not shown). In this manner, the described pivotability of the casing 15 is not impaired by interference through cables. The represented light head 12 has a curved form on its upper side, so that an oblique sloping contour of the casing 15 results with respect to the side surfaces of the casing, which makes it possible to reduce the distances of the light heads to a minimum in the installed state, so that they do not affect each other during pivoting.

Figure 6:
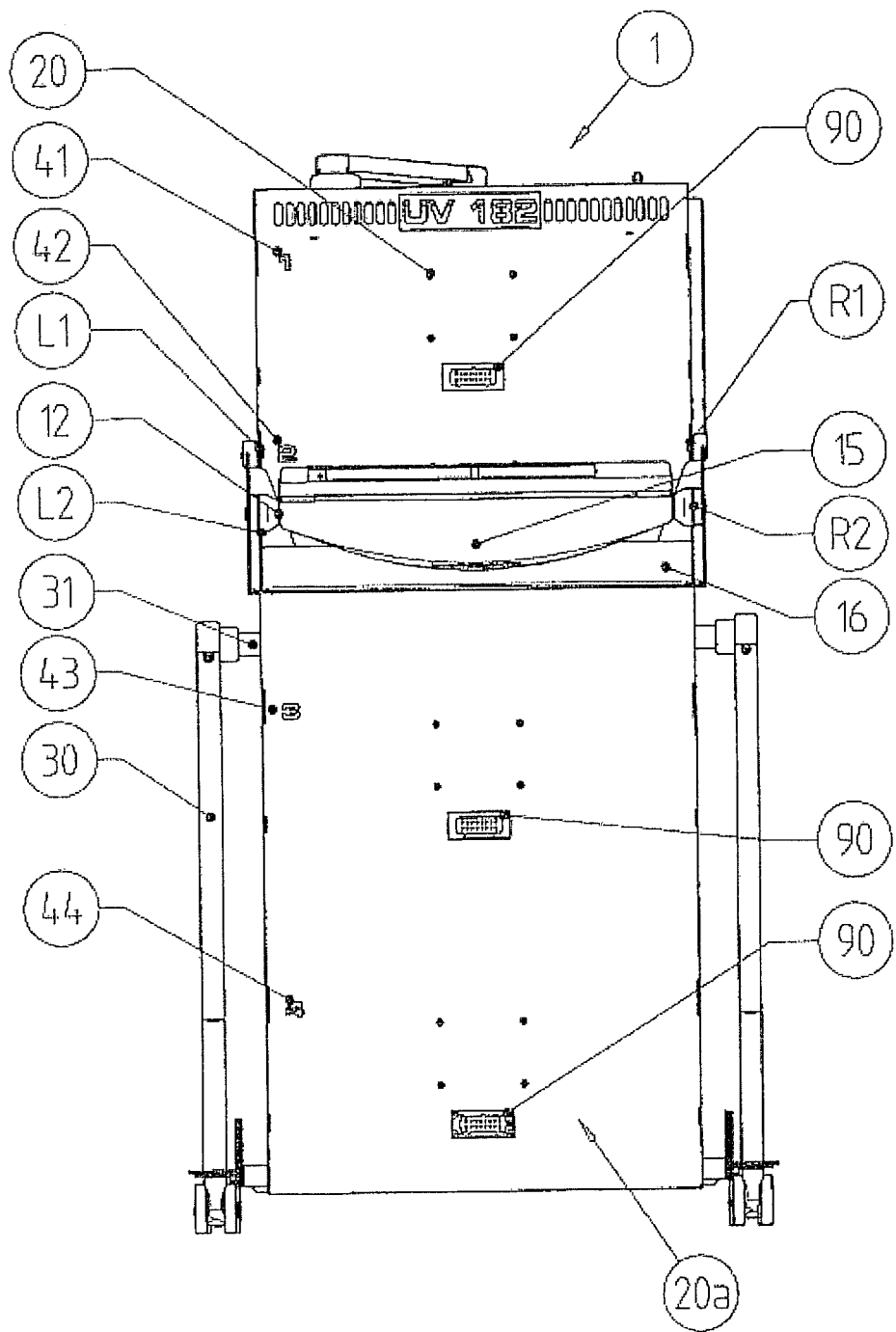
FIG. 6 is the irradiation device as taught by the invention as a front elevation with an installed light head.

FIG. 6 shows the irradiation device 1 as taught by the invention with merely one light head 12. What can be recognized is the essentially U-shaped design of the carrier system 30 as well as the first pivot axis 31 about which the control module 20 is pivoted. As already previously described, the front side 20a that is facing the patient of the control module 20 has four holders 41-44 for holding modularly designed light heads 11-14 (see FIG. 1), in which merely the second-from-the-top holder 42 is occupied with a light head 12.

Figure 7:
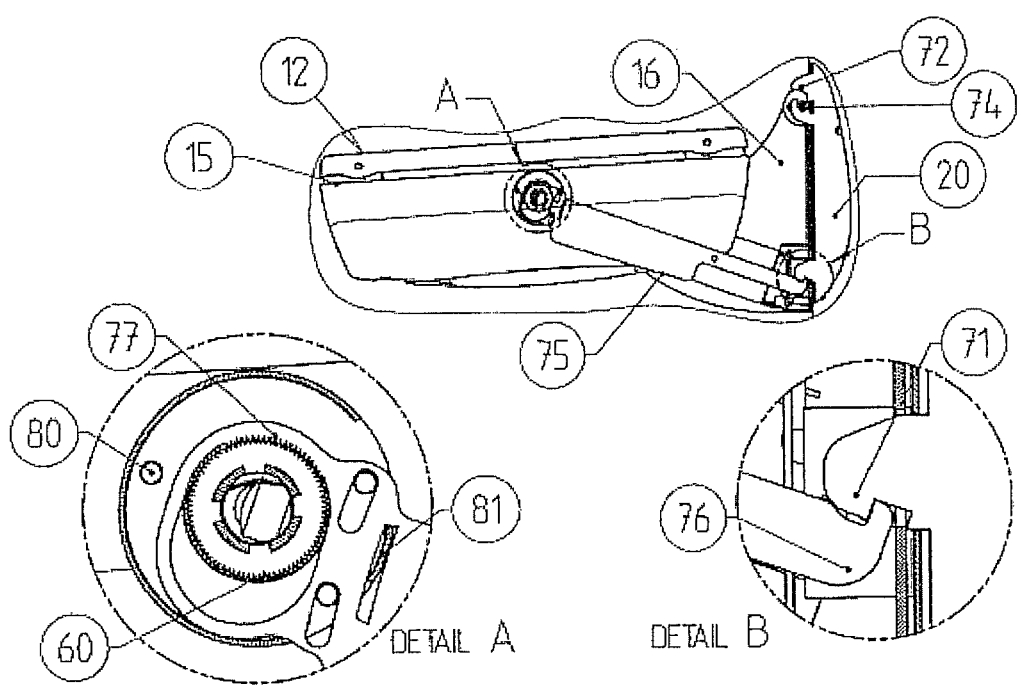
FIG. 7, with details A and B, is a lateral projection of a light head in the installed state, with a lateral detail view of a latching arrangement as well as a lateral detail view of a locking lever.
Figure 8:
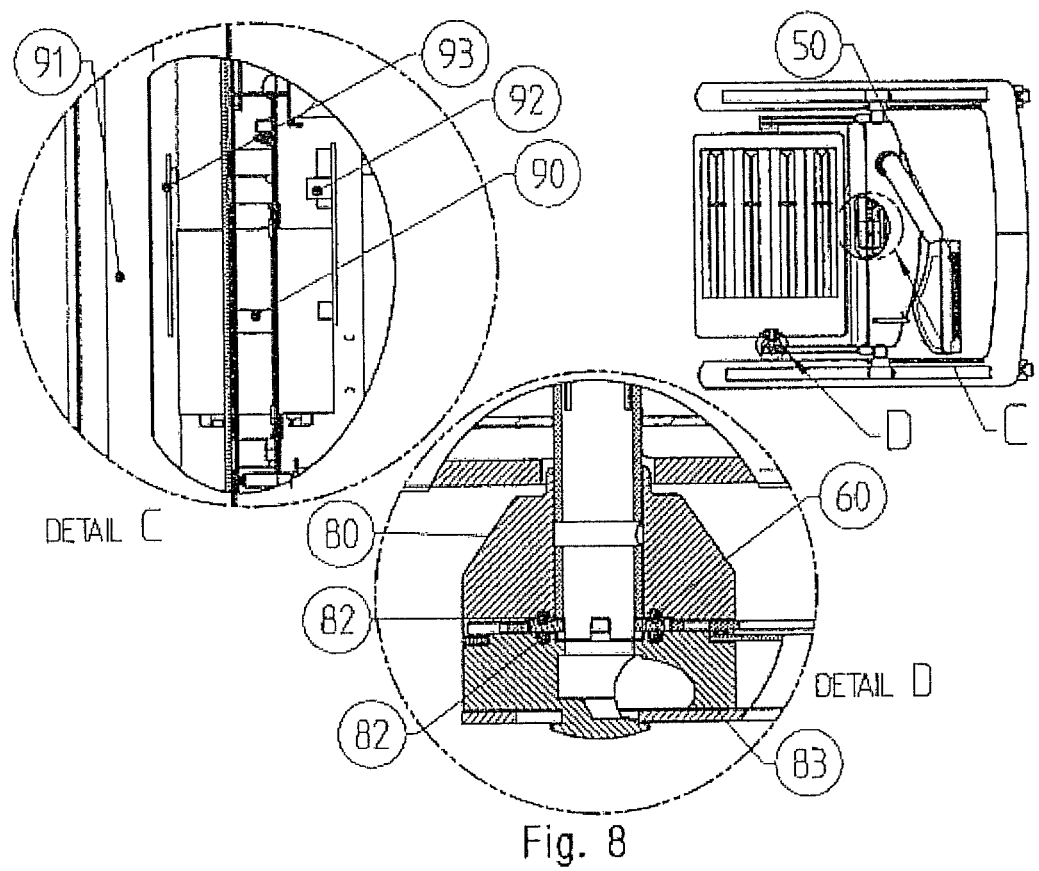
FIG. 8, with details C and D, is a horizontal projection of the irradiation device as taught by the invention with a cutaway detail view of the latching arrangement as well as a cutaway detail view of a contact connection of a light head with the irradiation device.

Also represented are contact connections 90 for electrical and/or communicative connection of the light heads with the control module 20 for controlling and/or transmission of information. Because of the previously described central arrangement of the controls of the light heads in the control module 20, in particular of the ballasts, the weight of the light heads 11-14 can be reduced significantly. Therefore units that can be handled well are created, which can be arranged easily on the control module 20. Arranging and removing and/or separating the light heads 11-14 from the control module 20 can preferably be performed without tools, so that an extremely flexible system is provided, which can be combined and adapted depending upon the individual requirement for the respective patient. In order to ensure safe operation, the light heads 11-14 must be securely attached on the control module 20 preventing them from being disconnected inadvertently. The same is applicable for the electrical connection of the light heads 11-14 with the control module 20. As already previously noted and represented in detail in FIGS. 6-8, the casing 15 of a light head is attached to the control module 20 by means of its supporting arm 16, wherein the supporting arm 16 is inserted into a section of the holder 42 that is designed as a slotted link with one pivot pin each in a left area L1 and a right area R1. Because of the rotation point 74 that is formed hereby, the supporting arm 16, due to the weight of the light head 12, performs a slewing motion down and automatically engages by means of a locking lever 75 into a lower detent link 71 of the control module 20, which represents a second section of the holder 42. This prevents inadvertent detachment of the connection between the light head 12 and/or its supporting arm 16 and the control module 20. The locking lever 75 preferably drops back into its detent position through its own weight.

Therefore, the user does not have to lock the light head 12 into place by having to undertake a separate locking step. This rather occurs automatically and can therefore not be forgotten. The force required for plugging-in the contact connection 90 between the supporting arm 16 and the control module 20 is likewise provided through the own weight of the light head 12, and corresponding contacting is therefore established automatically. The supporting him 16 is preferably designed as a U-shaped component, where the light head 12 is arranged between the two U-legs. The supporting him 16 can accordingly be connected with the control module 20 with its base section connecting the two legs. The contact connection 90 is likewise preferably integrated in the center of this base section of the supporting arm 15 and supported with a cover 91, thus preventing any contact with the contact connection 90 (see FIG. 8, detail C). For this arrangement it is necessary, however, to use a mating pair of connectors that does not have its own locking mechanism. This means that no separate locking mechanism apart from the detent mechanism of the locking levers has to be disconnected on the contact connection 90 when the respective light head is removed.

As represented in FIGS. 6-10, the housing 15 of the light head 12 is secured against twisting by means of a toothed lock washer 60 and a detent link 77 in an upper part of the locking lever 75. In the representative embodiment, merely the locking lever 75 on the right side (FIG. 7) is actually engaged in the detent link 77, so that it is possible to swivel the light head 12 using only one hand. Alternatively, the locking lever 75 of the left side can instead be engaged (not shown), or even both, whereas in the last case, a single-handed operation is no longer possible (both of the last mentioned cases are not shown).

In order to adjust an inclination angle of the casing 15 in the representative embodiment, the locking lever 75 on the right side R2 is pulled slightly to the top. The detent link 77 releases the toothed lock washer 60, and the casing 15 can be turned with the other hand. In this instance, the locking lever 75 must be retained, because it draws back into its original position because of its own weight and will cause automatic engagement. In order to enable this mode of operation, the locking lever 75 on the left side L2 is always disengaged by means of an asymmetric milling 81 on a bushing 80. This means that the toothed lock washer 60 is not engaged in the detent link 77. It is mainly provided for use of identical parts, but it could also be omitted or be replaced by components without teeth. The engagement in the lower detent link 71 on the switching element 20 in this case is nevertheless provided on both sides, however. In order to configure the adjustment motion smooth and cushioned, the toothed lock washers 60 can be inhibited on both sides by means of O-rings 82. The O-rings 82 are pressed against the toothed lock washers 60 by means of a screwed connection of the bushing 80 with the support 83.

Figure 9:
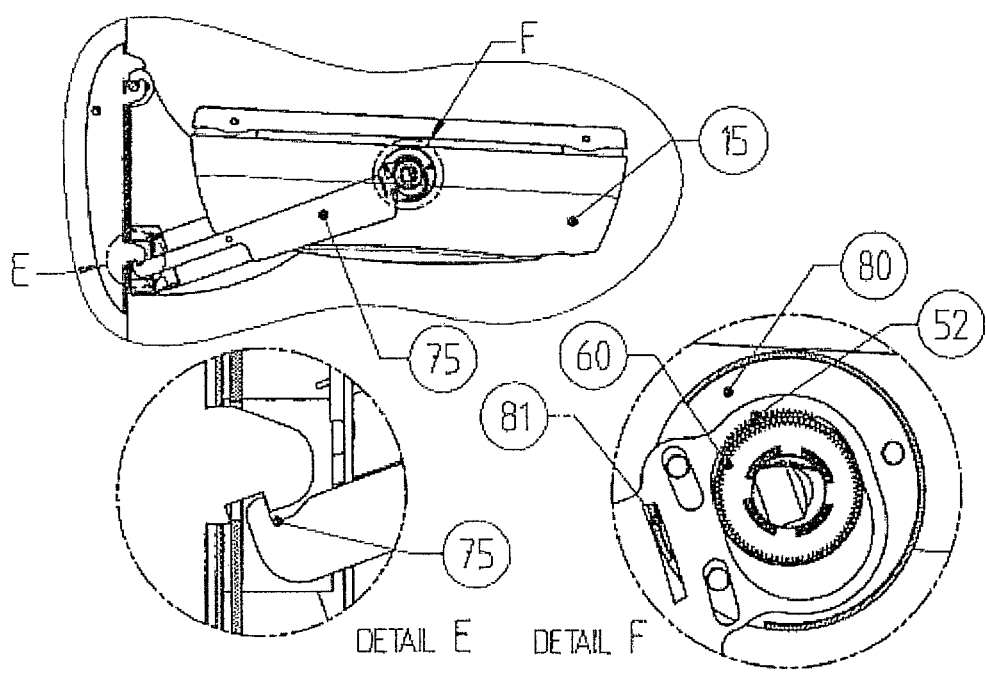
FIG. 9, with details E and F, is a further lateral view of the light head.
Figure 10:
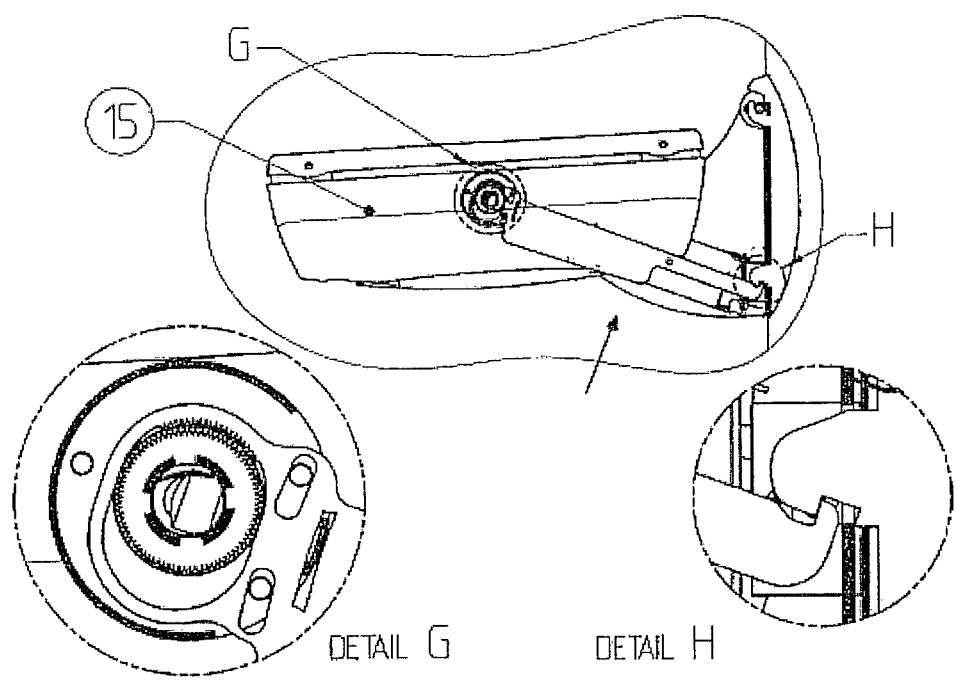
FIG. 10, with details G and H, is a further lateral view of the light head pursuant to FIG. 7 with the latching arrangement detached.
Figure 11:
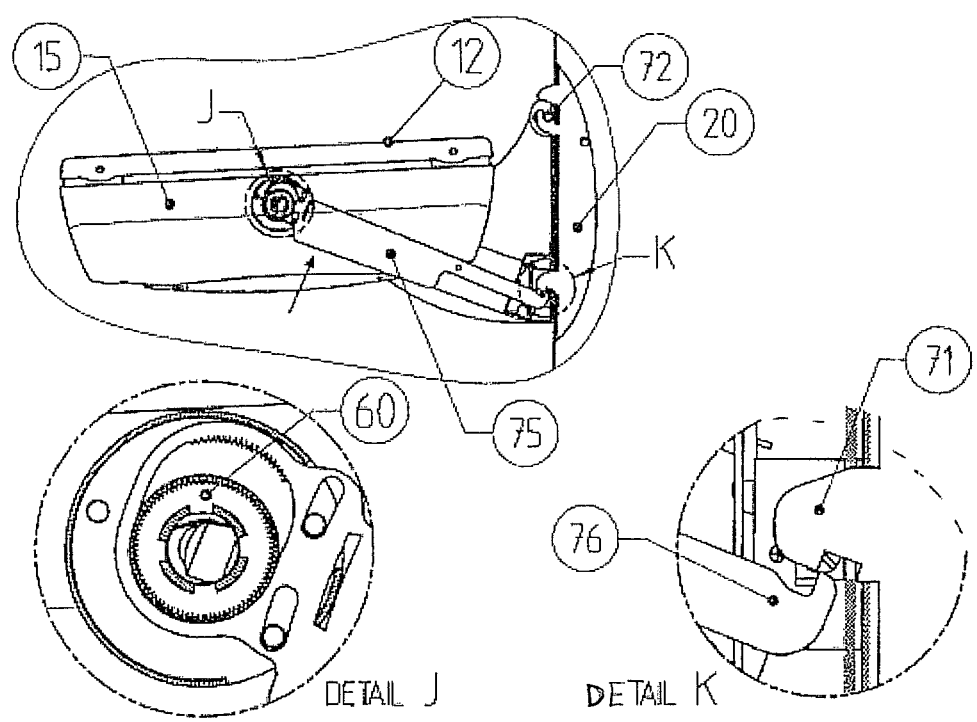
FIG. 11, and details J and K, and FIG. 12, with details L and M, are the light head according to FIGS. 9 and 10 in the unlatched state of the locking lever and the latching arrangement.
Figure 12:
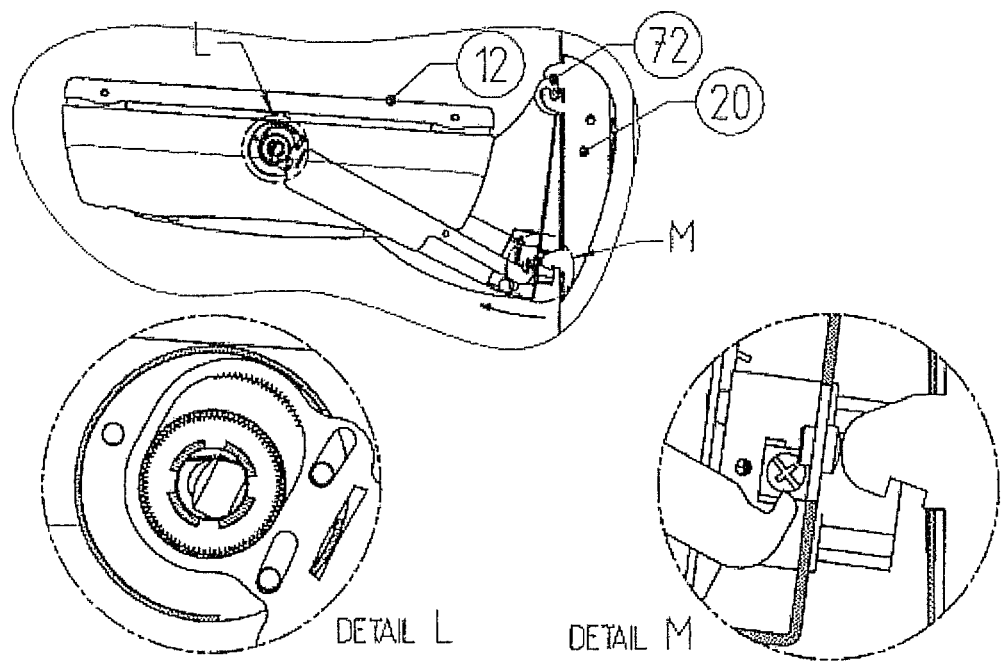

FIGS. 11 and 12 show the light head 12 according to FIGS. 9 and 10 in an unlatched stage of the locking lever 75 and the toothed lock washer 60. In order to separate the light head 11-14 from the control module 20, both locking levers 75 in the area of the casing 15 are completely pulled to the top. Latch lugs 76 which are arranged on an opposite end of the locking lever 75 are removed from the detent link 71 for this purpose. The light head 12 can subsequently be easily lifted away from the control module 20 with a swiveling motion and thereafter be removed from the section of the holder 72 that is formed as a slotted link.

Because of the represented possibility of unrestricted pluggability and combination options of the light heads and their various embodiments and component parts, in particular UV-A or UV-B sources of radiation, they must be identified at the respective plug-in places with the corresponding component parts. For this purpose, the control module 20 detects the respective light heads 11-14 as well as the selected holder. Each holder has a coding board 92 that is provided on the control module 20, so that a unique coding can be assigned. This is performed by means of jumpers, for example, which can be placed correspondingly. In addition, each light head 11-14 is preferably equipped with a storage medium 93, on which the light head 11-14 specifications are stored in duplicate. These specifications include the component parts of the lamp, for instance, intensity, operating time of the respective light head as well as its serial number. Each light head is therefore uniquely identifiable. This information is transmitted by means of a bus line in freely definable time intervals or during docking onto the control module 20, for example.

LIST OF REFERENCE SYMBOLS

1 Irradiation device
11 Light head
12 Light head
13 Light head
14 Light head
15 Casing
16 Supporting arm
17 Second pivot axis
20 Control module
21 Bearing
22 Vertical position
23 Pivoted position
24 Gearing
25 Gearing
30 Carrier system
30a Base
30b Leg
30c Brace
31 First pivot axis
41 Holders
42 Holders
43 Holders
44 Holders
50 Control element
51 Swivel arm
52 Control panel
Pivot axis
53 Third pivot axis
60 Toothed lock washer
71 Lower detent link
72 Lower holder
74 Rotation point
75 Locking lever
76 Latch lug
77 Detent link
80 Bushing
81 Milling
82 O-rings
83 Support
90 Contact connection
91 Cover 92 Coding board
93 Storage medium Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed:

1. An irradiation device, for irradiating parts of a patient during a use, comprising:
    a carrier system supporting said irradiation device away from an external support surface;
    a first and a second opposing leg member spaced apart and joined to a spanning foot member;
    said first and second opposing leg members extending away from said spanning foot member and defining a region therebetween;
    a first pivot axis defined between said first and second opposing leg members;
    a control module operatively mounted in a pivot arrangement about said first pivot axis in said region;
    said first pivot axis operatively enabling a securable pivoting of said control module from a first position perpendicular relative to said foot member to a second position inclined relative to said foot member;
    a plurality of light heads each with a respective light source;
    said light heads each detachably mounted on said control module; and
    a common control element system operatively controlling an operation of said control module during said use.

2. An irradiation device, according to claim 1, further comprising:
    at least one supporting arm operatively supporting each said light head;
    each said supporting arm being detachably connectable to a respective holder formed on said control module;
    each said light head being pivotably mounted on each said respective supporting arm each about a respective second pivot axis; and
    each said second pivot axis being spaced from and substantially parallel with said first pivot axis.

3. An irradiation device, according to claim 2, further comprising:
    an operative detachably connective information communication pathway between each said light head and said control module; and
    said common control element system in an operative control of respective light heads during said operation of said control module, whereby said common control element controls each respective light head during said use.

4. An irradiation device, according to claim 3, further comprising:
    a third pivot axis defined between said common control element system and said control module;
    said third pivot axis being substantially perpendicular to said first pivot axis and each respective said second pivot axis; and
    said common control element system swingable about said third pivot axis from a first position proximate said control module to a second position distal said control module.

5. An irradiation device, according to claim 4, wherein:
    said first pivot axis extends essentially through a center of gravity of said control module.

6. An irradiation device, according to claim 5, wherein:
    said control module is releasably engagable with said pivot arrangement during said use, whereby said control module is fixably positionable relative to said leg members.

7. An irradiation device, according to claim 6, further comprising:
    a releasable locking system between each said light head and said control module proximate said at least one supporting arm.

8. An irradiation device, according to claim 7, further comprising:
    a detent system operative to releasably fix each said light head relative to said control module.

9. An irradiation device, according to claim 8, further comprising:
    a plug-and-socket system operatively connecting respectively each said light head with said control module during said use.

10. An irradiation device, according to claim 1, wherein:
    said at least one light head is connected communicatively for exchange of information with said separate control module.

* * * * *